United States Patent [19]

Dobramysl et al.

[11] 4,408,045

[45] Oct. 4, 1983

[54] PROCESS FOR THE PREPARATION OF PARTIALLY ETHERIFIED METHYLOLMELAMINES

[75] Inventors: Wilhelm Dobramysl; Gerhard Stern; Walter Raml, all of Linz, Austria

[73] Assignee: Chemie Linz Aktiengesellschaft, Linz, Austria

[21] Appl. No.: 361,308

[22] Filed: Mar. 23, 1982

[30] Foreign Application Priority Data

Mar. 31, 1981 [DE] Fed. Rep. of Germany ....... 3112808

[51] Int. Cl.$^3$ ............................................. C07D 251/70
[52] U.S. Cl. .................................................... 544/196
[58] Field of Search ........................................ 544/196

[56] References Cited

U.S. PATENT DOCUMENTS

| 2,529,856 | 11/1950 | West et al. ........................ 260/676 |
| 2,715,619 | 8/1955 | Suen ................................... 260/676 |
| 2,918,452 | 12/1959 | Kun et al. ........................... 260/676 |
| 3,661,819 | 5/1972 | Koral et al. ........................ 544/196 |
| 3,679,589 | 7/1972 | Schnegelberger et al. ......... 544/196 |
| 3,915,973 | 10/1975 | Ribka et al. ........................ 544/196 |
| 4,101,520 | 7/1978 | Boldizar ............................. 544/196 |
| 4,163,835 | 8/1979 | Piesch ................................ 544/196 |
| 4,223,141 | 9/1980 | Hönel et al. ....................... 544/196 |

FOREIGN PATENT DOCUMENTS

| 17887 | 10/1980 | European Pat. Off. . |
| 2516349 | 10/1976 | Fed. Rep. of Germany . |
| 1030268 | 11/1964 | United Kingdom . |
| 1579416 | 11/1980 | United Kingdom . |

*Primary Examiner*—John M. Ford
*Attorney, Agent, or Firm*—Mark Dryer

[57] ABSTRACT

Process for the preparation of monomeric methylolmelamine which is partially etherified with methanol or ethanol and which contains at least 4 moles of formaldehyde per mole of melamine, by reacting melamine, paraformaldehyde and methanol or ethanol in a single stage reaction, the molar ratio of melamine to formaldehyde to alcohol being 1:5 to 10:6 to 20, in a virtually anhydrous medium, under a nitrogen atmosphere, at a pH of 7 to 8 and a temperature from 50° to 90° C. and with a reaction time of from 3 to 30 hours.

4 Claims, No Drawings

PROCESS FOR THE PREPARATION OF PARTIALLY ETHERIFIED METHYLOLMELAMINES

BACKGROUND OF THE INVENTION

1. Field of Invention

This invention relates to a process for the preparation of monomeric methylolmelamines which are partially etherified with methanol or ethanol and which contain at least 4 moles of formaldehyde per mole of melamine, in a one-stage reaction, without base catalysis for the methylolation reaction and without acid catalysis for the etherification reaction.

Compounds of this type are already known and have, for example, the following formula:

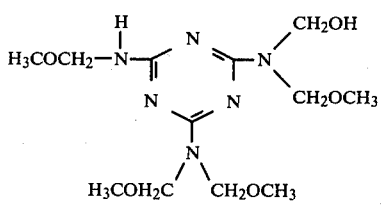

there being, on average, 4 to 5.5 moles of formaldehyde to 1 mole of melamine, and 1 to 4 methylol groups being etherified. This means that both the degree of methylolation and the degree of etherification of the compounds, which are obtained in the form of a mixture, may be different.

Compounds or mixtures of this type are employed, for example, in the manufacture of paints or textiles.

2. Description of the Prior Art

Numerous processes for the preparation of these compounds are already known; in these processes the methylolation is carried out under alkaline conditions; above all in order to achieve high degrees of methylolation, but the etherification is carried out at acid pH values. Examples of such processes are disclosed in U.S. Pat. Nos. 2,529,856 2,715,619 and 2,918,452, British Pat. Nos. 1,030,268 and 1,579,416, U.S. Pat. No. 4,223,141. Also European Patent Application No. 17,887, discloses a process in which strong acids must be present in the etherification stage and are preferred to fairly weak acids.

All the above prior art processes are carried out, at least in the methylolation stage, with the addition of water, which is in most cases introduced into the reaction mixture in the form of an aqueous formaldehyde solution or an aqueous alkali metal hydroxide solution.

European Patent Application No. 17,887 also discloses, inter alia, carrying out the reaction without the addition of water, which is recommended in cases where low degrees of condensation are desired. The etherified methylolmelamines thus obtained have the disadvantage that they have a considerable content of salt and also, as a result of hydrolysis, frequently contain acid constituents which impair their stability on storage because further condensation reaction to give resins is thereby promoted. This inadequate durability can be counteracted by rendering the mixtures alkaline for storage, which in turn increases the salt content even further and which can cause problems when processing, for example, in lacquers.

In addition to these two-stage processes, a one-stage process for the manufacture of etherified methylolmelamines is disclosed in German Auslegeschrift No. 2,516,349, in accordance with which melamine, formaldehyde and the alcohol used in the etherification stage are reacted in the presence of an acid at a pH value between 3 and 6.5, under elevated pressure and at a temperature within the range of 80° to 130° C. Besides the short reaction time, the advantage of this process is stated to be the production of products having fairly low degrees of methylolation. However, the disadvantage of the process is that even after quite short reaction times, high degrees of condensation occur, which cause the resins to have a limited solubility in water or to be completely insoluble in water. The tendency to cross-linking may be restrained only by extremely short reaction times of, for example, only 1 minute. The recommendation to carry out the reaction under anhydrous conditions is evidently not successful, as can be seen from the Examples. To avoid the stated high degrees of crosslinking, the same Applicant therefore has reverted to the two-stage procedure using alkaline methylolation, as is disclosed in European Patent Application No. 17,887.

SUMMARY OF THE INVENTION

An object of the present invention is to provide a process for the preparation of monomeric etherified methylolmelamines having a high degree of methylolation, in which process the troublesome salt content of the reaction products is avoided and their stability on storage is thereby increased, and in which it is also possible to dispense with the expensive 2-stage procedure.

Surprisingly, it has been found that this object may be achieved by carrying out both the etherification and the condensation reaction at a neutral pH and in the absence of acid and by avoiding the presence of appreciable quantities of water.

Salt-free mixtures of monomeric etherified methylolmelamines which do not require alkaline treatment to be stable on storage are thereby obtained.

Accordingly, the present invention provides a process for the preparation of a monomeric methylolmelamine which is partially etherified with methanol or ethanol and which contains at least 4 moles of formaldehyde per pole of melamine, which comprises carrying out, in a virtually anhydrous medium, a single stage addition reaction between formaldehyde, used as paraformaldehyde, and melamine and a simultaneous etherification reaction with methanol or ethanol, in a molar ratio of melamine:formaldehyde:alcohol of 1:5 to 10:6 to 20, under a nitrogen atmosphere at a temperature within the range of 50° to 90° C., a pH of 7 to 8 and a reaction time of from 3 to 30 hours, and subsequently evaporating the excess alcohol and formaldehyde.

The preferred melamine:formaldehyde:alcohol (i.e., methanol or ethanol) ratio is 1:6 to 8:8 to 12; the preferred reaction temperature is from 60° to 80° C. and the preferred reaction time is from 4 to 24 hours.

The process of the invention is carried out by mixing melamine, paraformaldehyde and methanol or ethanol and warming the mixture, while stirring. The sequence in which the components are added is not important. The paraformaldehyde used preferably contains approximately 95% by weight of total formaldehyde and preferably should not contain any free formic acid. The most important criterion is the pH value of the reaction solution, which should be from 7 to 8; this also excludes appreciable contamination caused by formic acid. The pH value is determined by diluting a sample of the reaction solution with water in a ratio of 1:10. Furthermore, all the reactions are carried out under a nitrogen atmosphere in order to prevent oxidation of the aldehyde by atmosphere oxygen, leading to the formation of formic acid. This ensures that no acid is present and that the products therefore do not have to be neutralized with alkali after the termination of the reaction. The products thus contain no extraneous salts and, therefore, they also do not require any alkaline treatment in order to increase their stability on storage.

As used herein "virtually anhydrous medium" means that the addition of water to the reaction mixture is omitted and that all the starting materials are employed in a concentrated form. Thus, paraformaldehyde is employed as the formaldehyde component, and pure alcohols which have been rendered anhydrous by distillation are employed as the alcohol component. However, small quantities of water, such as are present in commercially available paraformaldehyde, may be tolerated. Also, ethanol may be employed in 96% strength and does not have to be explicitly rendered absolutely anhydrous.

The initial molar ratio of melamine to formaldehyde is primarily the decisive factor for controlling the degree of methylolation (the degree of methylolation is the average number of moles of formaldehye, employed as paraformaldehyde, which undergo an addition reaction per mole of melamine). The greater this ratio, the higher is the degree of methylolation. At a melamine:formaldehyde ratio of 1:10, a maximum degree of methylolation of 5.5 can be achieved. A higher input of formaldehyde does not effect any appreciable increase in the degree of methylolation. At the preferred melamine:formaldehyde feed ratio of 1:6 to 8, degrees of methylolation of about 5.0 are obtained.

The products produced by the process of the invention are adequately stable and, even after one year, still exhibit the desired complete solubility in water. The lower limit of the melamine:formaldehyde ratio is 1:5.

Maintaining the virtually neutral, narrow pH range from 7 to 8, according to the invention, also affords the advantage that the etherification takes place under optimum conditions and that undesirable crosslinking reactions, which impair the solubility in water, do not take place.

The reaction time and temperature are of fairly low importance for the methylolation reaction, but these parameters are decisive for the degree of etherification (this is the average number of etherified methylol groups per mole of melamine). Long reaction times and high temperatures naturally produce high degrees of etherification. Long reaction times combined with a low temperature or short times and high temperatures produce similar degrees of methylolation and etherification. The melamine:alcohol molar ratio is less decisive; the only important factor is that the suspension should remain stirrable. It is interesting that the time taken to reach the clear point (that is to say up to the point at which the solution becomes clear) is prolonged by more alcohol.

The reaction also may be carried out under pressure at a fairly high temperature (80° to 90° C.), as a result of which the reaction times become correspondingly shorter.

Depending on the feed ratios and reaction conditions, it is possible that the solutions may not become completely clear. This slight turbidity does not affect the technical properties in use, but it may be filtered off in order to improve the visual impression.

After the termination of the reaction, the mixture is cooled to a temperature of 30° to 40° C. and the volatile constituents are removed under reduced pressure until the desired concentration is reached. This procedure may be carried out particularly advantageously using a thin-layer evaporator. The recovered solvent may be used without problems for the next batch.

The products prepared in accordance with the present invention exhibit excellent technical properties in use. They are miscible or soluble in water in all proportions. By virtue of the process of preparation, they contain no extraneous bases, acids or salts and are therefore very stable on storage. As a result of the free methylol groups, the products are more reactive than the completely etherified compounds. They exhibit their crosslinking properties even at fairly low temperatures and/or they require no catalyst for this purpose. Therefore, as mentioned above, they may be employed advantageously in the customary fields of application of methylolmelamines, such as, for example, in the manufacture of paints or textiles.

The following Examples illustrated the invention. In the Examples, percentage figures are percentages by weight.

The conditions for carrying out the reaction under a protective gas and for preparing samples, such as are described in Example 1, also apply to the other Examples.

EXAMPLE 1

40 g. of melamine, 73.9 g. of 95% strength paraformaldehyde and 108.5 g. of 99% strength methanol are charged to a 500 ml. four-necked flask equipped with a stirrer, a condenser, a thermometer and a gas inlet tube (pH value of the reaction mixture: 7.2; melamine:formaldehyde:methanol molar ratio 1:7.4:10.7). The apparatus is flushed with nitrogen and a slight excess pressure of nitrogen is provided during the whole reaction time. The mixture is warmed to 65° C. by means of a water bath and is kept at this temperature for 22 hours, while stirring. A clear solution is obtained, which is cooled to 40° C. and concentrated to the desired concentration. It can be used in this form. For analysis, 20 g. of an 85% strength colution in a 1 l. flask are freed from volatile constituents on a rotary evaporator under vacuum for two hours at 50° C. This gives a clear substance containing 24.5% of nitrogen and 45.2% of combined formaldehyde. The product can be diluted with water without any limiation. $H^1$-NMR analysis indicates a degree of methylolation of 5.0 and a degree of etherification of 2.9.

EXAMPLE 2

The reaction is carried out analogously to Example 1, but the batch is kept a 80° C. for 8 hours and is then, as before, brought to the desired concentration. A small quantity is, as before, freed from volatile constituents on a rotary evaporator and is analyzed. This gives a clear product which can be diluted with water in all proportions and contains 23.6% of nitrogen and 43.6% of combined formaldehyde. $H^1$-NMR analysis indicates a degree of methylolation of 5.0 and a degree of etherification of 2.6.

EXAMPLE 3

As described in Example 1, 48 g. of melamine is reacted with 79 g. of 95% strength paraformaldehyde in 91.5 ml. of 99% strength methanol (pH value of the reaction mixture 7.9; melamine:formaldehyde:methanol molar ratio 1:6.6:6.0). The reaction is carried out for 3.5 hours at 70° C. The solution is filtered while hot, concentrated and then cooled. At room temperature the product is highly viscous and can be diluted with water without any limitation. Analysis indicates 25.7% of nitrogen and 43.7% of combined formaldehyde. The $H^1$-NMR spectrum indicates a degree of methylolation of 4.9 and a degree of etherification of 1.6.

EXAMPLE 4

48 g. of melamine and 66.2 g. of 95% strength paraformaldehyde are reacted, as in Example 1, in 134 g. of 99% strength methanol (pH value of the reaction mixture 7.5; melamine:formaldehyde:methanol molar ratio 1:5.5:11). The reaction mixture is kept at 70° for 6.5 hours. A fairly thick turbidity is filtered off. After the solvent has been removed under vacuum, a product containing 29.7% of nitrogen and 42.0% of combined aldehyde is obtained. The $H^1$-NMR spectrum indicates a degree of methylolation of 4.2 and a degree of etherification of 1.2.

EXAMPLE 5

48 g of melamine, 114.3 g. of paraformaldehyde and 305 ml. of methanol, corresponding to a melamine:formaldehyde:methanol ratio of 1:9.5:20, are reacted as in Example 1, the pH value of the mixture being 7.3. This reaction mixture is kept at 70° C. for 20 hours, and, after being evaporated, gives a product which can be diluted with water without any limitation and which contains 22.5% of nitrogen and 43.0 % of combined formaldehyde. The $H^1$-NMR spectrum indicates a degree of methylolation of 5.5 and a degree of etherification of 3.7.

EXAMPLE 6

48 g. of melamine and 88.8 g. of paraformaldehyde in 189 g. of 96% strength ethanol are reacted at 80° to 85° C. for 6.5 hours in the apparatus of Example 1 (pH value of the reaction mixture 7.9; melamine:formaldehyde:ethanol molar ratio 1:7.4:10.7). Removal of the solvent gives a product containing 22.1% of nitrogen and 39.9% of combined formaldehyde. Evaluation of the $H^1$-NMR spectrum indicates a degree of methylolation of 5.1 and a degree of etherification of 2.1.

EXAMPLE 7

295 g. of melamine, 490 g. of 95% strength paraformaldehyde and 800 g. of 99% strength methanol are kept at between 70° and 90° C. for 2.5 hours in a 2.5 l. autoclave equipped with a stirrer (pH value of the reaction mixture 7.5; melamine:formaldehyde:methanol molar ratio 1:6.6:10.7). This gives a clear, colorless product which, after removal of the solvent, contains 24.9% of nitrogen and 45% of combined formaldehyde. The $H^1$-NMR spectrum indicates a degree of methylolation of 5.0 and a degree of etherification of 2.7.

EXAMPLE 8

17 kg. of melamine, 28.4 kg. of 95% strength paraformaldehyde and 46.5 kg. of 99% strength methanol are charged to a 100 l. kettle, warmed to 70° C. and kept at this temperature for 6 hours until clear solubility is achieved (pH value of the reaction mixture 7.5; melamine:formaldehyde:methanol molar ratio 1:6.7:10.8). The excess solvent is then removed by vacuum distillation at 48° C. until the desired concentration is reached. As described in Example 1, a small quantity is freed from volatile constituents on a rotary evaporator and is analyzed. This gives a product containing 25.2% of nitrogen and 45.4% of combined aldehyde. The substance can be diluted with water in all proportions. $H^1$-NMR analysis indicates a degree of methylolation of 4.9 and a degree of etherification of 2.2.

We claim:

1. A process for the preparation of a monomeric methylolmelamine which is partially etherified with methanol or ethanol and which contains at least 4 moles of formaldehyde per mole of melamine, which comprises carrying out, in a virtually anhydrous medium, a single stage addition reaction between formaldehyde, used as paraformaldehyde, and melamine and a simultaneous etherification reaction with methanol or ethanol, in a molar ratio of melamine:formaldehyde:alcohol of 1:5 to 10:6 to 20, under a nitrogen atmosphere at a temperature within the range of 50° to 90° C., a pH of 7 to 8 and a reaction time of from 3 to 30 hours, and subsequently evaporating the excess alcohol and formaldehyde.

2. A process according to claim 1, in which the melamine:formaldehyde:alcohol ratio is 1:6 to 8:8 to 12.

3. A process according to claim 1, in which the reaction temperature is 60° to 80° C.

4. A process according to claim 1, in which the reaction time is from 4 to 24 hours.

* * * * *